US006993803B2

(12) United States Patent
Chan

(10) Patent No.: US 6,993,803 B2
(45) Date of Patent: Feb. 7, 2006

(54) ELECTRIC TOOTHBRUSHES AND PACKAGES CONTAINING SAME

(75) Inventor: John G. Chan, Loveland, OH (US)

(73) Assignee: Church & Dwight Co., Inc., Princeton, NJ (US)

( * ) Notice: Subject to any disclaimer, the term of this patent is extended or adjusted under 35 U.S.C. 154(b) by 171 days.

(21) Appl. No.: 10/189,647

(22) Filed: Jul. 3, 2002

(65) Prior Publication Data

US 2003/0221983 A1 Dec. 4, 2003

Related U.S. Application Data

(63) Continuation-in-part of application No. 10/158,037, filed on May 30, 2002, now abandoned.

(51) Int. Cl.
*A61C 17/22* (2006.01)
(52) U.S. Cl. .......................................... 15/22.1; 15/28
(58) Field of Classification Search ................ 206/361, 206/362.2, 461, 470; 15/22.1, 28, 22.2, 22.4, 15/23, 24, 29; 200/60, 318.2, 551
See application file for complete search history.

(56) References Cited

U.S. PATENT DOCUMENTS

| 1,437,476 A | 12/1922 | Paine |
| 1,471,185 A | 10/1923 | Miller |
| 1,475,584 A | 11/1923 | Humeston |
| 1,527,972 A | 3/1925 | Gallagher |
| 1,541,877 A | 6/1925 | Voorhees |
| 1,774,722 A | 9/1930 | Officer |
| 1,785,868 A | 12/1930 | Koretzky |
| 1,902,590 A | 3/1933 | Shannon |
| 1,903,947 A | 4/1933 | Stimson |
| 2,132,218 A | 10/1938 | Officer et al |
| 2,138,387 A | 11/1938 | Officer et al. |
| 2,420,585 A | 5/1947 | Crimmins |
| 2,445,635 A | 7/1948 | Poliakoff |
| 2,599,295 A | 6/1952 | Thomas |
| 3,220,543 A | 11/1965 | McCord et al. |
| 3,221,115 A | 11/1965 | Feher, Jr. |
| 3,226,502 A | 12/1965 | Schotz |
| 3,249,725 A * | 5/1966 | Hutt et al. ................... 200/551 |
| 3,851,126 A | 11/1974 | Keller |

(Continued)

FOREIGN PATENT DOCUMENTS

CA 1053633 5/1979

(Continued)

*Primary Examiner*—Luan K. Bui

(57) ABSTRACT

An actuator assembly and packaging feature for an electric toothbrush is disclosed. The actuator assembly includes a positionable member accessible along the outer surface of the toothbrush body. The actuator assembly further includes a spring member retained within the interior of the toothbrush body which urges a cam member against the underside of the positionable member. The positionable member defines an aperture extending through its midsection within which is disposed a depressible member. The depressible member has an outer end which is also accessible along the outer surface of the toothbrush body. Upon pressing the depressible member, the cam member and spring are urged against an electrical circuit provided within the body of the toothbrush which is used to selectively operate a motor and drive mechanism to move one or more sets of bristles. The actuator assembly additionally includes a feature of providing a raised region along an outer surface of the positionable member which guards against accidental or unintentional depressing of the depressible member. The packaging feature relates to a member formed in a package cover that is suitably sized and positioned over the depressible member of the actuator so that the cover, when pressed, may momentarily activate the toothbrush within the package.

12 Claims, 4 Drawing Sheets

U.S. PATENT DOCUMENTS

| | | |
|---|---|---|
| 3,992,596 A | 11/1976 | Miller |
| 4,025,743 A | 5/1977 | Oswald |
| 4,897,517 A | 1/1990 | Gundlach |
| 5,494,252 A | 2/1996 | Amit et al. |
| 5,504,959 A * | 4/1996 | Yukawa et al. ............... 15/22.1 |
| 5,590,434 A | 1/1997 | Imai |
| 5,718,335 A | 2/1998 | Boudreaux |
| 5,883,346 A | 3/1999 | Stöcken |
| 5,969,309 A | 10/1999 | Nishimura et al. |
| 6,000,083 A | 12/1999 | Blaustein et al. |
| 6,046,414 A | 4/2000 | Hirschfeld |
| 6,059,106 A | 5/2000 | Baker et al. |
| 6,178,579 B1 | 1/2001 | Blaustein et al. |
| 6,189,693 B1 | 2/2001 | Blaustein et al. |
| 6,288,352 B1 | 9/2001 | Fukui et al. |
| 6,311,837 B1 | 11/2001 | Blaustein et al. |
| 6,360,395 B2 | 3/2002 | Blaustein et al. |
| 6,371,294 B1 | 4/2002 | Blaustein et al. |
| 6,564,940 B2 * | 5/2003 | Blaustein et al. ........ 206/362.2 |

FOREIGN PATENT DOCUMENTS

| | | |
|---|---|---|
| CH | 220038 | 3/1942 |
| DE | 1085589 | 7/1960 |
| DE | 29618648 | 10/1996 |
| EP | 0691107 | 1/1996 |
| EP | 0796766 | 9/1997 |
| EP | 0892418 | 7/1998 |
| EP | 0886293 | 12/1998 |
| GB | 524905 | 8/1940 |
| GB | 1167444 | 10/1969 |
| JP | 10-127345 | 5/1998 |

* cited by examiner

ELECTRIC TOOTHBRUSHES AND PACKAGES CONTAINING SAME

This is a continuation-in-part (CIP) application of U.S. application Ser. No. 10/158,037, filed May 30, 2002 abandoned.

FIELD OF THE INVENTION

The present invention relates to the field of toothbrushes, and more particularly, the invention relates to the field of electrically powered toothbrushes, and actuators and packaging therefor.

BACKGROUND OF THE INVENTION

Electric toothbrushes typically utilize a switch accessible along the exterior or body of the toothbrush that controls operation of the toothbrush. Generally, such switches have two positions, one position in which the toothbrush is not operating or "off" and another position in which the toothbrush is activated or "on." Generally, these switches are slidable or otherwise linearly displaceable between these two positions. Such position switches have also been modified to also activate their corresponding circuits or mechanisms upon being pushed or depressed. This pushbutton feature may be provided in combination with the previously noted linear position function in a single switch.

Most consumer goods and particularly those that relate to health and beauty are packaged in retail-friendly display cartons such that the product that is being sold may be readily viewed by a consumer contemplating its purchase. Such packaging is currently used for many different brands and models of commercially available electric toothbrushes.

Multi-motion electric toothbrushes are known which are believed to provide superior cleaning efficacy. These toothbrushes often provide multiple brushing motions by two or more brush heads. In addition to the superior cleaning action, the operation of the brush and complex motion of the brush heads often generates interest in a potential purchaser of the toothbrush. That is, many consumers find the operation of the brush to be interesting to watch.

As a result of this phenomenon, the assignee of the present invention previously developed a package for an electric toothbrush that was adapted for retail display and enabled a consumer to activate the toothbrush while sealed within the package. Accordingly, an interested consumer could simply activate a packaged toothbrush by pushing the switch of the toothbrush through its packaging. Some such arrangements are shown in commonly assigned U.S. Pat. Nos. 6,311,837; 6,189,693; and 6,178,579, the substances of which are incorporated herein by reference.

A significant problem with such consumer friendly packaging is that the toothbrush may accidentally be activated during shipment or storage. Furthermore, it is neither practical nor economical to include actuation interlocks in the packaging or to somehow "arm" or selectively enable actuation of the toothbrush prior to retail display.

Accordingly, there is a significant need for an electric toothbrush that may utilize current retail packaging approaches and may be activated after packaging, yet which would not be prone to accidental or unintended activation particularly while in its package.

SUMMARY OF THE INVENTION

The present invention achieves all of the foregoing objectives and provides, in a first aspect, a packaged electric toothbrush comprising a package having a cover, a back, and a cavity defined therebetween. The package cover includes a projection that extends from an interior face of the cover. The packaged toothbrush also comprises an electric toothbrush disposed within the cavity of the package. The toothbrush includes a housing, a neck, and a head. The housing has a motor and a power source for energizing the motor. The motor is engaged with a movable bristle holder disposed on the head. The electric toothbrush also includes a first movable member which may be moved between two positions. The electric toothbrush is energized when the movable member is in the second position. The first movable member has a second movable member that is slideably disposed within the first member. The second movable member is movable in a direction that is substantially perpendicular to the direction of movement of the first movable member. The second movable member is positioned adjacent the projection extending from the interior face of the cover. The electric toothbrush may also be energized by applying a force upon the package cover near the projection to thereby cause the projection to contact and depress the second movable member when the first movable member is in its first position.

In yet another aspect, the present invention provides a packaged electric toothbrush comprising a package having a cover that defines a hollow interior within the package. The cover has an outwardly directed outer face and an oppositely directed inner face. The inner face has a projection extending from the inner face into the hollow interior of the package. The packaged electric toothbrush also comprises an electric toothbrush disposed within the hollow interior of the package. The toothbrush includes an actuator assembly positioned adjacent the projection of the cover. The actuator assembly has a first slidable component and a second depressible component residing within an aperture defined in the first slidable component. The electric toothbrush is momentarily activated by pressing the cover and causing the projection extending from the inner face to contact and depress the depressible component of the actuator assembly.

In a further aspect, the present invention provides a method for momentarily activating an electric toothbrush disposed within a package. The electric toothbrush has an actuator for preventing accidental or unintended activation. The actuator includes a first slidable component disposed on a housing of the toothbrush. This slidable component defines an aperture within which is disposed a depressible component configured such that upon depressing the depressible component within the aperture, the electric toothbrush is activated. This method includes a step of providing a projection extending from an inwardly directed face of the package. The projection is positioned alongside the depressible component and sized to fit within the aperture defined in the slidable component. The method also includes a step of pressing the package in the proximity of the actuator such that the projection contacts the depressible component and thereby activates the electric toothbrush.

BRIEF DESCRIPTION OF THE DRAWINGS

The present invention may take form in various components and arrangements of components, and in various techniques, methods, or procedures and arrangements of steps. The referenced drawings are only for purposes of illustrating preferred embodiments, they are not necessarily to scale, and are not to be construed as limiting the present invention.

It is believed that the present invention will be better understood from the following description taken in conjunction with the accompanying drawings in which.

DETAILED DESCRIPTION OF THE PREFERRED EMBODIMENTS

Reference will now be made in detail to various embodiments of the present invention, examples of which are illustrated in the accompanying drawings. One aspect of the present invention is an electric toothbrush having an improved actuator assembly. The electric toothbrush can be disposed within a package and operated in a momentary fashion while in the package. The actuator assembly can be used with a wide variety of electric toothbrushes, including electric toothbrushes having replaceable heads and electric toothbrush heads having one or more movable bristle holders. The actuator assembly can be used in combination with electric toothbrushes having drive mechanisms that rotate, oscillate, or reciprocate (as well as combinations thereof) to impart motion to the one or more bristle holders. In addition, the present invention actuator can be used in combination with electric toothbrushes and electric toothbrush heads where the drive mechanism is operatively connected to multiple bristle holders or only one of the bristle holders. In the latter instance, the bristle holders may themselves be interconnected so that a motion is imparted to the bristle holder that is not directly coupled to the shaft.

A wide variety of electric toothbrushes and drive mechanisms are described in U.S. Pat. Nos. 5,617,603; 5,850,603; 5,974,615; 6,032,313; 5,732,432; 5,070,567; 5,170,525; 5,416,942; 3,588,936; 5,867,856; and 4,397,055, the substances of which are incorporated herein by reference. The present invention actuator assembly can be utilized in conjunction with any of these brush types as well as others.

Figure 1:
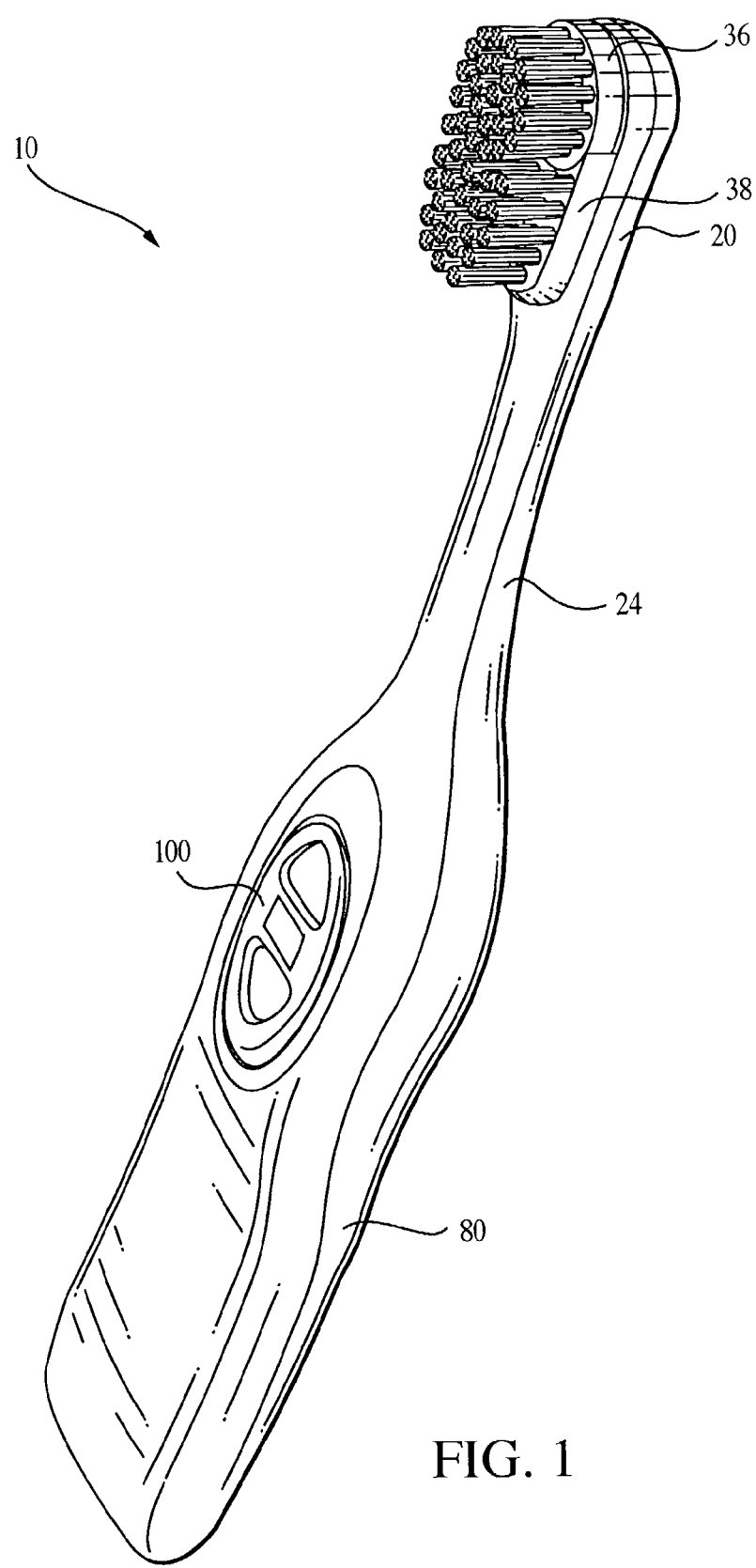
FIG. 1 is a perspective view of a toothbrush using a preferred embodiment actuator in accordance with the present invention.

FIG. 1 illustrates a preferred embodiment electric toothbrush 10 comprising a toothbrush head 20, a body or housing 80, and an elongated neck 24 extending therebetween. The body or housing 80 generally extends along an axis generally referred to herein as the longitudinal axis of the body. This axis is sometimes referred to herein as the longitudinal axis of the toothbrush. The body or housing 80 is hollow and includes a motor 23 and batteries 25 for powering the motor 23. A rechargeable power source can be substituted for the batteries. A drive mechanism (not shown) is housed at least partially within the neck 24. The toothbrush 10 further comprises an actuator assembly 100 for selectively controlling the operation of the motor and drive mechanism. A first bristle holder 36 is disposed along the head 20. While the first bristle holder 36 is illustrated as circular in shape, other shapes can be utilized. Further, while the first bristle holder 36 is disposed at the end of the head 20, it will be appreciated that the bristle holder 36 can be disposed away from the first end and other features, such as stationary bristles, might be disposed between the first bristle holder 36 and the distal end of the head 20.

A second bristle holder 38 is disposed adjacent the first bristle holder 36. While it is desirable to locate the second bristle holder 38 directly adjacent the first bristle holder 36, it is contemplated that a gap may be provided between the first and second bristle holders. In addition, the gap between the first and second bristle holders might be filled with stationary bristles which are embedded in a fixed or stationary third bristle holder (not shown) which forms part of the toothbrush head. Further, while the first bristle holder 36 has been described as adjacent the first end of the head 20, it is contemplated that the second bristle holder 38 might be disposed adjacent the first end of the head 20. It is further contemplated that the toothbrush may only utilize one movable bristle holder in combination with one or more groups of fixed bristles. The bristles disposed within the bristle holders can be arranged in any manner known in the art.

In addition, the electric toothbrush 10 of FIG. 1 could be provided with a replaceable head. A suitable arrangement that can be utilized with the present invention actuator is disclosed in U.S. Pat. No. 5,617,601, the substance of which is incorporated herein by reference.

FIGS. 2–5 illustrate in greater detail a preferred embodiment actuator assembly 100 according to the present invention. The actuator assembly can energize the toothbrush 10 in one of two manners or modes. In the first mode, the toothbrush is operated in a momentary manner within its package to demonstrate operation of the toothbrush. In a second mode, the toothbrush 10 is operated in a longer or continuous mode for brushing of one's teeth.

Figure 3:
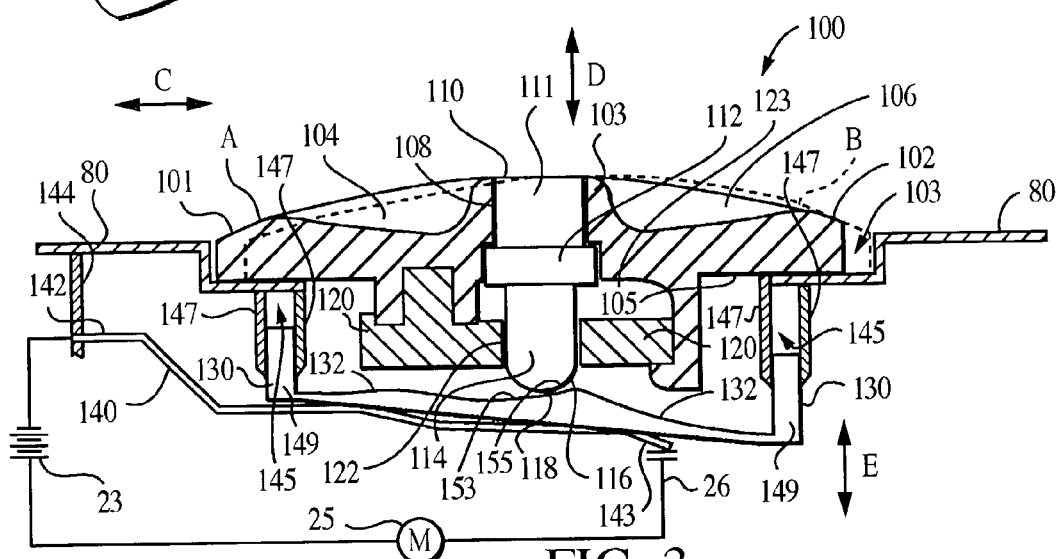
FIG. 3 is a cross-sectional side view taken across line 3—3 in FIG. 2 illustrating the preferred embodiment actuator and its assembly and incorporation within an electric toothbrush, wherein the positionable member is shown in the "A" position.
Figure 4:
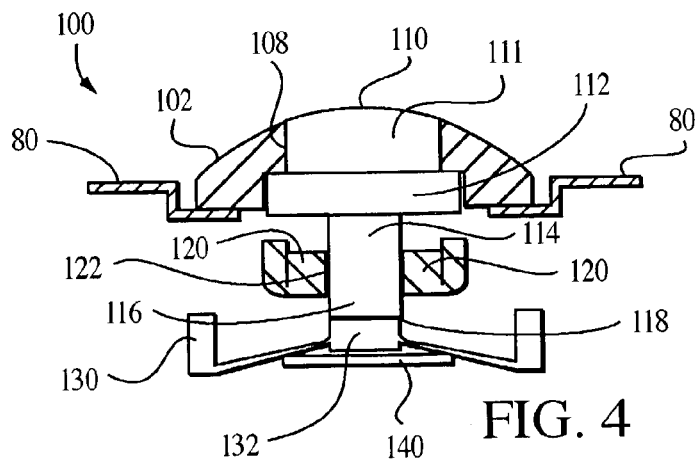
FIG. 4 is a cross-sectional view of the preferred embodiment actuator taken along line 4—4 in FIG. 2, further illustrating the assembly and aspects of the preferred embodiment actuator.

The actuator assembly 100 comprises a first movable or positionable switch member 102 that has an outer face 101 accessible along an outer surface of the body or housing 80 of the toothbrush. The positionable member 102 may be moved between positions "A" and "B," in the direction of arrow "C" such as shown in FIG. 3. When the member 102 is in the "A" position, the brush is off, and when in the "B" position, the brush is on. This is described in greater detail. The positionable member 102 is slideably disposed within a recess 103 of the housing 80. The positionable member 102 also has an oppositely directed base face 105 that is disposed adjacent to and is provided at least partially in sliding contact with a floor of the recess 103. The face 105 is directed toward the interior of the toothbrush body or housing 80. The outer face 101 preferably defines one or more depressed regions such as regions 104 and 106 that facilitate gripping and engagement by a user's fingers with the positionable member 102. The positionable member 102 also provides a raised region 103 extending outwardly from the outer face 101 of the positionable member 102. Defined within the raised region 103 is an aperture 108. The raised region 103 is preferably located near the aperture 108 defined in the positionable member. Most preferably, the raised region 103 extends around the entrance to the aperture 108 defined along the outer face 101. The raised region can either completely encircle the aperture 108 or only partially encircle the aperture 108. For example, the raised region can be provided as a continuous wall around the aperture 108 or as a series of discrete walls.

The outer face 101 of the positionable member may exhibit a variety of shapes and forms. Furthermore, it is contemplated to include a colored coating or paint or other decorative material along the outer face of the positionable member. For some applications, it may be desirable to include a water resistant or water proof liner over the entire outer face 101 of the positionable member 102. In this embodiment, it would be preferred to seal the outer edges or periphery of the liner to the housing or body 80 of the toothbrush.

The positionable member 102 may also include an auxiliary guide member 120, preferably located along its underside and preferably adjacent the base face 105. The guide member 120 defines an aperture 122 directly in line with the aperture 108 defined in the positionable member 102. Accordingly, the two apertures 108 and 122 are aligned and readily receive a depressible member 110 described below.

The actuator assembly 100 also comprises an electrically conductive spring member 140 disposed within the body or housing 80 of the toothbrush and generally proximate or adjacent to the positionable member 102. The spring member 140 is in electrical contact on one side with batteries 23 and can be placed in electrical contact with a motor 25. Preferably, the spring member 140 is proximate or adjacent to the base face 105 of the positionable member 102. The spring member 140 has a first end 142 preferably engaged or otherwise secured to the housing or body of the toothbrush by an extension 144 that extends from the housing 80. The opposite end 143 of the spring member 140 is preferably free and cantilevered from the first end 142. In FIG. 3, the spring member 140 is shown in its undeflected state resulting in an open electrical circuit with the batteries 23 and motor 25.

The actuator assembly 100 further comprises a second movable or depressible switch member 110 disposed in the positionable member 102. Thus, the actuator assembly 100 comprises two principal pieces that are movable by a user of the toothbrush 10: (i) the positionable member 102 which moves substantially along the longitudinal axis of the toothbrush 10, such as in the direction of arrow "C," and (ii) the depressible member 110 slideably disposed within the positionable member 102 that moves substantially perpendicular to the longitudinal axis of the toothbrush 10 or generally perpendicular to the direction of travel of the positionable member 102. The direction of movement of the depressible member is illustrated in FIG. 3 as arrow "D." In addition, the depressible member 110 moves with positionable member 102 along the housing 80 when the positionable member 102 is moved by a user. The depressible member 110 includes an outer end 111 that is generally accessible from the outer surface or exterior of the toothbrush housing 80. The depressible member 110 also includes an interior end 114 opposite from the outer end 111, and which is disposed within the housing of the toothbrush. Moreover, the depressible member 110 preferably includes a retaining ring 112 extending about its periphery and generally between the outer end 111 and the interior end 114. The retaining ring is preferably sized so as to retain the depressible member 110 within or with the positionable member 102. In the event the guide member 120 is utilized, the depressible member 110, and preferably the interior end 114 of the member 110 extends through the aperture 122 defined in the member 120. The respective alignment of the aperture 108 in the positionable member 102 and the aperture 122 in the member 120 assist in maintaining proper orientation of the depressible member 110. Further, the retaining ring 112 is captured between the guide member 120 and the positionable member 102 within a cavity 123 formed by the guide member 120 and the positionable member 102 so as to retain the depressible member 110 with the actuator assembly 100.

The depressible member 110 may be in nearly any form or shape. For instance, the member 110 may utilize a cross section, i.e. taken perpendicular to the longitudinal axis of the member 110, that is circular, rectangular, oval, or other shape as desired. However, the preferred shapes of the apertures 108 and 122 defined in members 102 and 120, respectively, depend upon the cross-sectional shape of the depressible member 110. For example, if the depressible member 110 utilizes a circular cross-sectional shape, then the preferred shape of the apertures 108 and 122 is circular. Similarly, the span or interior dimensions of the apertures 108 and 122 must be sufficient to allow the depressible member 110 to move within those apertures, yet not be so great that the member 110 is not held in its proper orientation, described below.

Figure 5:
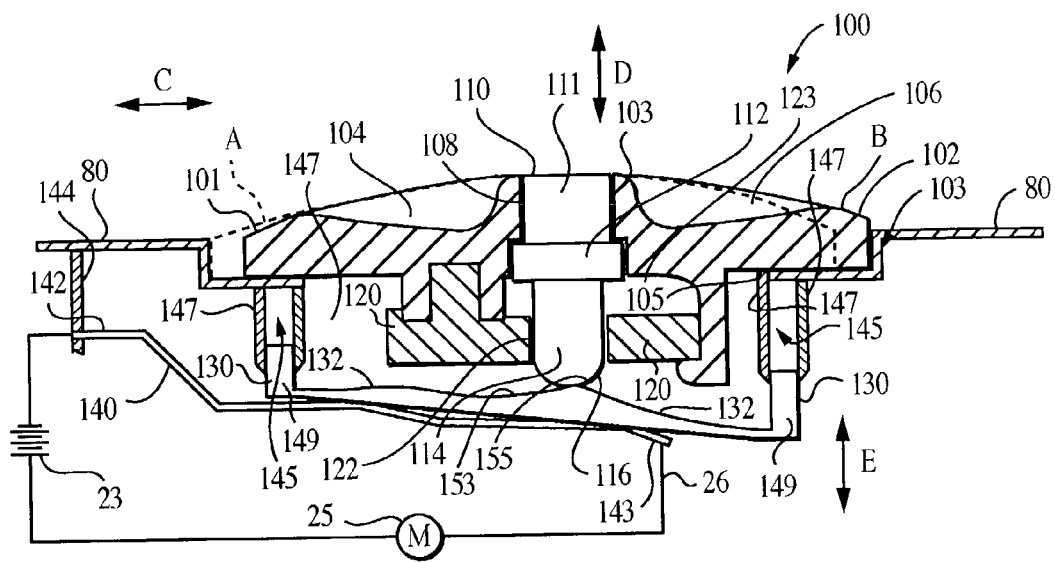
FIG. 5 is a cross-sectional side view of the actuator assembly of FIG. 3, wherein the positionable member is shown in the "B" position.

The actuator assembly 100 additionally comprises a cam member 130 engaged with the spring member 140. The cam member 130 is captured at each end within tracks 145 which are each formed by a pair of flanges 147 that depend from the housing 80. The upturned ends 149 of the cam member 130 are slideably received within the tracks 145 so that the cam member 130 is able to move substantially perpendicular with respect to the longitudinal axis of the toothbrush 10 (i.e., in a direction in and out of the housing 80 rather than along the housing 80). Stated another way, the cam member 130 moves in substantially the same direction as the depressible member 110. The direction of movement of the cam member 130 is illustrated in FIG. 3 by arrow "E." The cam member 130 includes a cam surface 132 directed toward the base face 105 of the positionable member 102 and the interior end 114 of the depressible member 110. As best illustrated in FIGS. 3 and 5, the cam member has a thickness that may vary at one or more locations along the length of the cam member. The variation in thickness corresponds to the desired profile of the cam surface 132. This is explained in greater detail herein.

The interior end 114 of the depressible member 110 includes a rounded end 116 having a tip or tapered region 118 that contacts the cam surface 132. In some applications, it may be desirable to form the rounded end 116 to have a semicircular shape when viewed in a cross section taken parallel to the longitudinal axis of the depressible member 110. It will be appreciated that decreasing the amount of surface area contact between the interior end 114 of the member 110 and the cam surface 132 generally results in the positionable member 102 being easier to move back and forth along the housing of the toothbrush. It is also contemplated to apply or otherwise deposit an effective amount of a friction reducing material along the cam surface 132.

The spring member 140 maintains a biasing force against the cam member 130 so that the cam surface 132 engages the interior end 114 of the depressible member 110. This in turn maintains an outward biasing force on the depressible member 110 so that it is pushed upward away from the housing to its maximum possible extent (i.e., to the point where the retaining ring 112 of the depressible member 110 engages the positionable member 102). During the first mode of operation of the toothbrush 10 when the positionable member 102 is in position "A", a force can be applied to the outer end 111 of the depressible member 110, such as by a user's finger, that overcomes the biasing force of the spring member 140. This causes the interior end 114 of the depressible member 110 to push the cam member 130 downward (i.e., in a direction toward the interior of the housing 80) and causes cam member 130 to move away from the base face 105 thereby pushing the cantilevered spring member 140 into electrical contact with a contact 26 to close the electrical circuit with the motor 25 and energize the motor 25. During this downward movement of the cam member 130, the free end 143 of the spring member 140 is pivoted or moved about the fixed end 142 of the spring member 140. In this manner the toothbrush 10 can be energized so long as a force is applied to the depressible member 110 against the bias of the spring member 140. Other arrangements of the cam member and/or spring member are contemplated. For example, the spring and cam members can be combined into a single integral component.

Figure 2:
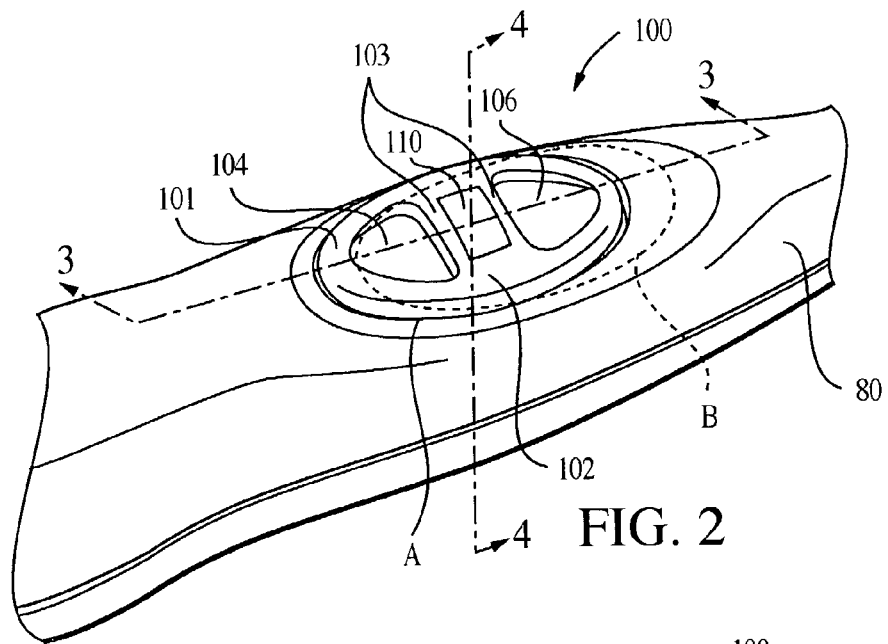
FIG. 2 is a partial perspective view detailing a preferred embodiment actuator in accordance with the present invention.

For the second mode of operation of the electric toothbrush 10, the relationship of the cam member 130, and particularly the orientation and inclination of the cam surface 132, determines the amount of linear movement required by the positionable member 102 before the cam member 130 moves the free end 143 of the spring member 140 to close the electrical circuit and energize the motor 25. That is, the relative position of the free end 143 of the spring 140, i.e. at contact 26, in the second mode of operation, depends upon the position of the member 102. So, if the positionable member 102 is in position "A" as shown in FIGS. 2 and 3, the action of the spring 140 urges the cam member 130 toward the base face 105 until the interior end 114 of the depressible member 110 contacts the cam member 130. In this position, the electrical circuit is open, i.e. at contact 26, until either the depressible member 110 is depressed as previously described (the first mode of operation) or the positionable member 102 is moved to the "B" position, as shown in FIG. 5 (the second mode of operation). When the positionable member 102 is moved to the "B" position, the rounded end 116 is moved to a location along the cam member 130 which is thicker than the location of the cam member 130 at which the rounded end 116 is located when the positionable member 102 is in the "A" position. This thicker cross-section causes the cam member 130 to move downwardly thereby pushing the free end 143 of the spring member 140 into electrical contact with the contact 26 to energize the motor 25 when the positionable member 102 is displaced in a direction generally parallel with a longitudinal axis of the toothbrush body as generally shown by arrow C (i.e., linearly displaced along the housing 80). When in the "B" position, the positionable member 102 in combination with the depressible member 110 force the cam member 130 (and in turn the spring member 140) downward to close the electrical circuit without continued application of a force by the user of the electric toothbrush 10.

The actuator assembly 100 may further be provided with one or more detents or favored positions for the positionable member 102. One detent is defined by the valley 153 of the cam surface 132. The rounded end 116 of the depressible member 110 rests within the valley 153 when the positionable member 102 is in position "A". The inclined surface 155 which forms part of the valley 153 prevents accidental movement of the positionable member 102 to the "B" position as some of the biasing force of the spring member 140 must be overcome to move the positionable member to the "B" or "on" position. This arrangement can prevent accidental actuation of the toothbrush 10 when it is in its package. Thus, when the positionable member 102 is in position "A" such that the rounded end 116 of the depressible member 110 is disposed within the valley 153 of the cam surface 132, the motor 25 can be energized only by depressing the depressible member 110 and only for so long as the depressible member 110 is depressed. When the positionable member 102 is in position "B", the motor 25 is energized so long as the positionable member 102 is in position "B". The depressible member 110 need not be depressed and a continual force need not be applied to the positionable member to keep it in the "B" position.

In accordance with another aspect of the present invention, the raised region 103 of the positionable member 102 that generally surrounds the outer end 111 of the depressible member 110, extends outward from the toothbrush body 80 a distance sufficient to preclude unintentional depressing of the member 110. Specifically, it is preferred that the raised region 103 extends outward from the toothbrush body 80 a distance that is equal to or greater than the maximum distance of the outer end 111 of the member 110 from the toothbrush body 80.

The components of the actuator assembly may be formed from nearly any suitable material including but not limited to plastics, metals, and composite materials. It is generally preferred that the spring be formed from a suitable metal that exhibits sufficient flexibility and memory so that the spring 130 maintains a force upon the depressible member 110 to keep that member extending outward from the toothbrush body 80. If the spring is formed from a material other than metal, it may be necessary to provide some type of electrically conductive material, e.g. in the form of a metal layer, liner, or foil, along the region of the spring that may serve as a switch for the electrical circuit governing operation of the toothbrush.

Figure 6:
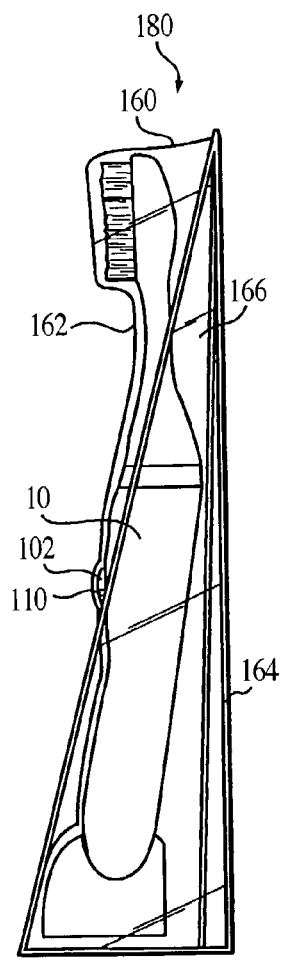
FIG. 6 is a side elevational view of a preferred embodiment electric toothbrush disposed within a package in accordance with the present invention.

Referring to FIG. 6, in which a packaged toothbrush product 180 is illustrated, the electric toothbrush 10 can be placed within a package 160 so that the depressible member 110 can be depressed through the package. The package 160 comprises a cover 162 and a back 164. The cover 162 has an outwardly directed outer face and an oppositely directed inner face. A cavity 166 containing the toothbrush 10 can be formed between the cover 162 and the back 164. The electric toothbrush is oriented within the package 160 so that the positionable member 102 is closely disposed next to a portion of the cover 162 so that a potential purchaser of the toothbrush 10 can depress the depressible member 110 while the electric toothbrush 10 is still within the package 160. This permits a demonstration by momentary actuation of the toothbrush 10 while it is still within the package 160. Once the electric toothbrush 10 is removed from the package 160, the positionable member can be moved to the "B" or "on" position for continual, rather than momentary, actuation of the electric toothbrush 10. The cover 162 can optionally incorporate one or more of the recesses described in U.S. Pat. No. 6,311,837, the substance of which is incorporated herein by reference. While it is desirable for the depressible member 110 to be depressed by depressing the cover 162, it is contemplated that other arrangements can be implemented to allow depression of the depressible member 110 while the electric toothbrush 10 is within the package 160. For example, the cover 162 might have a cutout or hole that matches the size and shape of the depressible member 110 so that the latter can be actuated directly by the user without depressing the cover 162. Additionally, it will be appreciated that the present invention includes packaged toothbrush products utilizing other types of electric toothbrushes besides toothbrush 10.

Figure 7:
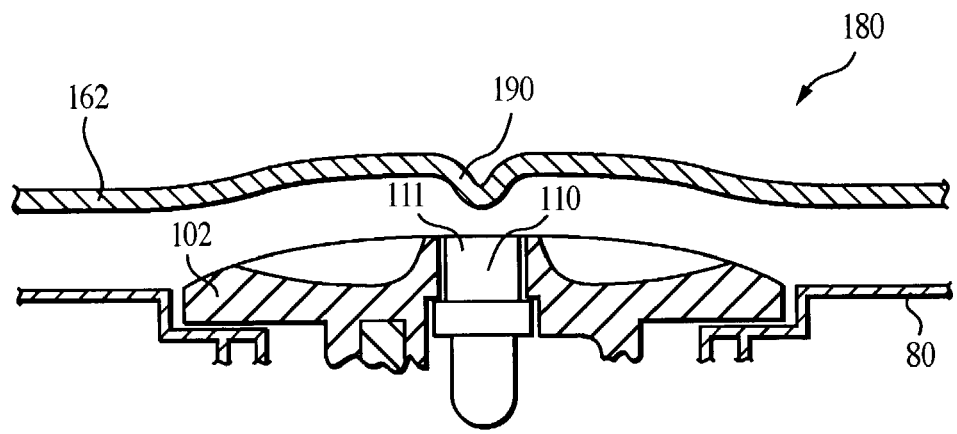
FIG. 7 is a partial cross-sectional view of the actuator assembly, similar to that illustrated in FIG. 3, of the preferred embodiment electric toothbrush disposed within a package according to the present invention.
Figure 8:
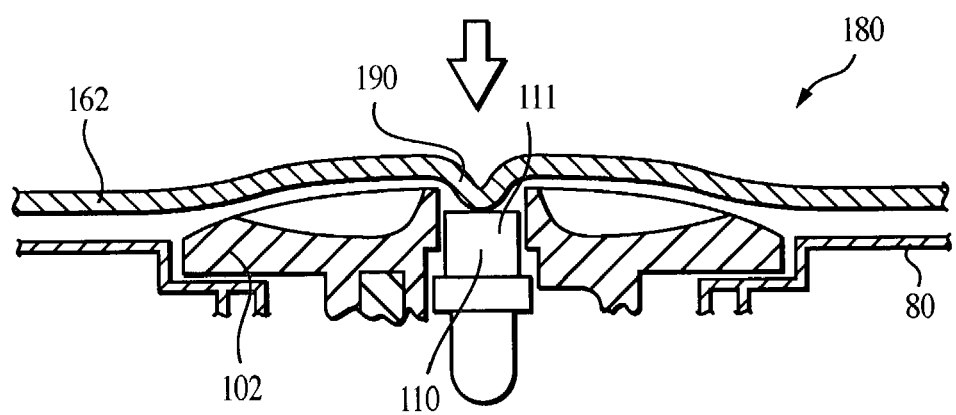
FIG. 8 is a partial cross-sectional view of the package and actuator assembly, illustrating momentary actuation of the toothbrush by depressing the package against the actuator assembly.

FIGS. 7 and 8 illustrate in greater detail momentary actuation of the actuator assembly of the packaged toothbrush product 180 shown in FIG. 6. These figures are a partial cross-sectional view of the assembly illustrated in FIG. 3, and the orientation and positioning of a projection 190 formed in a cover 162 of the packaged product 180. It will be noted that a projection 190 is formed along the cover 162 and that the projection 190 is aligned directly over the depressible member 110 of the actuator assembly. The projection 190 preferably provides a raised region or other protuberance that extends from the interior or inward facing surface of the cover 162. The packaged toothbrush may be momentarily actuated by applying a force to the package cover 162 such that the projection 190 contacts the outer end 111 of the depressible member 110 and displaces the member 110 into the interior of the assembly as previously described herein. It will be appreciated that the projection 190 is sized so as to fit within the same channel within which the depressible member 110 resides. It is contemplated that the projection 190 may be in a variety of forms and not limited to the particular embodiment shown in FIGS. 7 and 8. Preferably, the projection 190 is formed of the same material as the cover. Most preferably, the projection 190 is integrally formed with the cover such as by molding.

The present invention also relates to a technique of momentarily activating an electric toothbrush while it is still packaged, and particularly, a toothbrush using the preferred embodiment actuator assembly as described herein. This technique is performed by providing the preferred embodiment toothbrush 10 having the preferred embodiment actuator assembly 100 and appropriately positioning the toothbrush within a package. The package features the use of a cover, preferably a transparent front cover to enable the toothbrush to be visible from the package exterior. Most preferably, the package includes an inwardly directed projection, such as projection 190, that is positioned near a depressible member of an actuator assembly of the toothbrush. The projection is sized so as to fit within the channel within which the depressible member resides. By pressing the cover, in the region of the projection, against the depressible member, that member momentarily activates the toothbrush.

The present invention has been described with reference to particular embodiments. Modifications and alterations will occur to others upon reading and understanding this specification. It is intended that all such modifications and alternations are included insofar as they come within the scope of the appended claims or equivalents thereof.

I claim:

1. An electric toothbrush, comprising:
a housing, a neck, and head, wherein said housing has a motor and a power source for energizing said motor, said motor operatively connected to a movable bristle holder disposed on said head;
a first movable member movable along said housing between a first position and a second position, wherein the electric toothbrush is energized when said first movable member is in said second position;
said first movable member having a second movable member slideably disposed therein, wherein said second movable member is movable in a direction substantially perpendicular to the movement of said first movable member, wherein said electric toothbrush is energized by depressing said second movable member when said first movable member is in said first position; and
wherein an outer face of said second moveable member is substantially flush with an outer face of said first moveable member.

2. The electric toothbrush of claim 1, wherein said first movable member includes a raised region along said outer surface.

3. The electric toothbrush of claim 2, wherein said raised region generally extends adjacent an aperture defined in said first movable member.

4. The electric toothbrush of claim 3, wherein said raised region extends entirely around an entrance to said aperture.

5. The electric toothbrush of claim 2, wherein said raised region extends outward from said housing of the toothbrush a distance that is equal to or greater than the maximum distance of the outer end of said second movable member from said housing.

6. The electric toothbrush of claim 1, further comprising a spring disposed within said housing proximate said first movable member, said spring having a first end engaged to said housing and a second free end opposite from said first end.

7. The electric toothbrush of claim 6, further comprising a cam that engages said spring and is movable therewith.

8. The electric toothbrush of claim 7, wherein said spring urges said cam toward said first movable member.

9. The electric toothbrush of claim 7, further comprising a guide member disposed between said first movable member and said cam, said guide member defining a second aperture within which is disposed said second movable member.

10. The electric toothbrush of claim 1, wherein said second movable member includes a retaining ring disposed between said outer end and said interior end of said second movable member.

11. The electric toothbrush of claim 1, wherein said first movable member and said second movable member may be linearly displaced in a direction generally parallel to a longitudinal axis of said housing.

12. The electric toothbrush of claim 1, wherein said second movable member is movable in a direction generally perpendicular to the direction of displacement of said first movable member.

* * * * *